US005597379A

United States Patent [19]
Haines et al.

[11] Patent Number: 5,597,379
[45] Date of Patent: Jan. 28, 1997

[54] METHOD AND APPARATUS FOR FEMORAL RESECTION ALIGNMENT

[75] Inventors: Timothy G. Haines; David B. Goldstein, both of Hoboken, N.J.

[73] Assignee: Hudson Surgical Design, Inc., Rutherford, N.J.

[21] Appl. No.: 342,143

[22] Filed: Nov. 18, 1994

Related U.S. Application Data

[63] Continuation-in-part of Ser. No. 300,379, Sep. 2, 1994.

[51] Int. Cl.[6] .................................................. A61B 17/56
[52] U.S. Cl. ............................... 606/80; 606/88; 606/90; 606/96
[58] Field of Search .................................. 606/90, 88, 79, 606/80, 82, 86, 87, 89, 96, 102; 600/201, 210

[56] References Cited

U.S. PATENT DOCUMENTS

| | | |
|---|---|---|
| 4,457,307 | 7/1984 | Stillwell . |
| 4,474,177 | 10/1984 | Whiteside . |
| 4,487,203 | 12/1984 | Androphy . |
| 4,501,266 | 2/1985 | McDaniel .............. 606/90 X |
| 4,566,448 | 1/1986 | Rohr, Jr. . |
| 4,567,886 | 2/1986 | Petersen ................ 606/88 X |
| 4,586,496 | 5/1986 | Keller . |
| 4,653,488 | 3/1987 | Kenna . |
| 4,721,104 | 1/1988 | Kaufman et al. . |
| 4,722,330 | 2/1988 | Russell et al. . |
| 4,736,737 | 4/1988 | Fargle et al. . |
| 4,787,383 | 11/1988 | Kenna . |
| 4,892,093 | 1/1990 | Zarnowski et al. ......... 606/82 |
| 4,896,663 | 1/1990 | Vandewalls ................ 606/79 |
| 4,938,762 | 7/1990 | Wehrli ..................... 606/88 |
| 5,002,545 | 3/1991 | Whiteside et al. ......... 606/80 |
| 5,047,032 | 9/1991 | Jellicoe ................... 606/83 |
| 5,049,149 | 9/1991 | Schmidt ................... 606/87 |
| 5,053,037 | 10/1991 | Lackey .................... 606/79 |
| 5,098,436 | 3/1992 | Ferrante et al. .......... 606/88 |
| 5,234,432 | 8/1993 | Brown .................... 606/79 |
| 5,250,050 | 10/1993 | Poggie et al. ........... 606/79 |

*Primary Examiner*—Guy Tucker
*Attorney, Agent, or Firm*—Friscia & Nussbaum

[57] ABSTRACT

The apparatus of the present invention includes a number of components including a guide body component, an extension block component, a rotating arm component, an extension rod component, and a tibial referencing component. The guide body component contacts the distal-most surface of the femur. Its location is based off of the posterior femoral condyles and the surface of the distal-most femoral resection or the unresected distal-most femoral surface. The rotating arm component is interconnected with the guide body and may rotate with respect thereto, thus allowing for the direct or indirect adjustment of the rotating alignment of cutting guides for resecting the distal femur. The rotating arm component carries arms with drill screw apertures which direct placement of drill holes in the femur which are used to attach a cutting guide to the femur. The rotating arm component is attached to the extension rod component which extends to the tibial referencing component which references the location and orientation of the proximal resected surface of the tibia. Thus the rotating alignment of the distal femoral prosthesis is established with respect to the orientation of the resected proximal tibial surface.

29 Claims, 10 Drawing Sheets

METHOD AND APPARATUS FOR FEMORAL RESECTION ALIGNMENT

RELATED APPLICATIONS

This application is a continuation-in-part application of copending U.S. patent application Ser. No. 08/300,379, filed Sep. 2, 1994, still pending, the entire disclosure of which is incorporated herein by reference.

BACKGROUND OF THE INVENTION

1. Field of the Invention

This invention generally relates to a method and apparatus for establishing the rotational alignment of the resected distal surfaces of a human femur with respect to the proximal tibia to permit proper rotational orientation and the anterior and posterior location of drill holes in the distal femur for attaching a cutting block for resecting the distal human femur.

2. Description of the Prior Art

Different methods and instruments have been developed to enable a surgeon to resect a human distal femur to attach a distal femoral prosthesis to the distal femur. Keeping in mind the ultimate goal of the procedure is to restore the knee joint to normal function, it is critical that the implant's location and orientation be consistent with the state of the ligaments, tendons and other soft tissue remaining in the knee joint after completion of the surgery.

It is common to use the central axis of the femur, the posterior and distal femoral condyles, and/or the anterior distal femoral cortex as guides to determine the location and orientation of the distal femoral resections. The location and orientation of these resections are critical in that they dictate the final location and orientation of the distal femoral implant. It is commonly thought that the location and orientation of the distal femoral implant are the most critical factors in the success or failure of the artificial joint.

Past efforts have not been successful in consistently and properly locating and orienting distal femur resections. Such efforts are set forth in the following patents, none of which teach or suggest all of the benefits and advantages of the patents.

Androphy, U.S. Pat. No. 4,487,203, discloses a knee resection system comprising a guide member, femur and tibia guide rods, a tibia adaptor, a tibia bar, and a femur bar for establishing equal flexion and extension gaps. The guide member block receives a femur guide rod inserted into a femur. A guide rod extends in a vertical direction from the guide member block. When aligned with the femur, pins are pushed through the guide member block, to fix the guide member block with respect to the distal femur. Then, the distal femoral condyles are resected with an oscillating saw through guide slots in the guide member block. A guide member block is then attached to a tibia guide rod extending into the tibia, the tibia guide rod having a second guide at a right angle thereto for receiving the guide member block. The guide member block is then positioned by means of a tibia bar and, when properly aligned, is fixed to the anterior side of the proximal tibia with pins. The tibia is then resected with an oscillating saw inserted through slots in the guide member block. Next the flexion gap between the resected proximal tibia and the resected posterior distal femur is determined by turning the guide rod inserted into the femur to orient the perpendicular section towards the tibia to identify the distance between the tibia and the femur with the collateral ligaments extended taughtly. Then, the knee is placed in extension, the guide member block is placed onto the guide rod, and the guide member block is positioned along an extension of the femur block. When properly aligned, guide member pins are pressed to secure the guide member to the distal femur. The knee is then placed in flexion and the distal femur is resected with an oscillating saw inserted through slots in the guide member block.

Rohr, Jr., U.S. Pat. No. 4,566,448 discloses a ligament tensor device having a first member to engage the tibia and a second member to engage the intercondylar notch of a femur and a means for moving the second means with respect to the first means for applying a selected tension to the ligaments of the joint. Additionally, the invention includes cutting guide slots for guiding the cutting of the femoral condyles. A pressure plate is placed on the sectioned surface of the tibia. The pressure plate is interconnected with a cutting guide head which is contacted by a threaded screw extending from the support housing structure. The support housing structure is movable with respect to the tibia cutting guide head by means of the screw member. The support housing structure is attachable to the tibia to move to the femur away from the tibia to tension the ligaments of the knee structure. The femur may be resected through cutting slots on the support housing structure.

Kenna, U.S. Pat. No. 4,653,488 and U.S. Pat. No. 4,787,383 discloses holes drilled into the distal femur and a femoral cutting jig attached thereto. The femoral cutting jig is attached with lock-in pins to the femur. An axial alignment guide is used to establish the proper varus-valgus and flexion extension alignment of the distal femoral cuts. A guide pin extends from the long axial alignment guide and the pin is properly positioned when it is parallel to the femoral shaft. The distal femoral cutting jig is positioned accordingly and locked into place with a jig having teeth for engagement with the femur. Rotation, medial-lateral and anterior-posterior orientation of the femoral prosthesis is determined by a femoral drill jig having two posterior skids (or tongs) which are slid between the posterior femoral condyles and the tibial plateaus. The jig contains two holes for use in making the holes for the femoral prosthesis fixation studs. A cutting jig may then be attached for making anterior and posterior femoral cuts. To achieve correct tibial axial alignment, longitudinal traction is applied to the foot to bring the tibial shaft parallel to an alignment pin. Then the transverse tibial cut may be made.

Russell, et al, U.S. Pat. No. 4,722,330 discloses distal femoral surface guide for mounting on an intramedullary alignment guide for use in shaping the distal femoral surface. A conventional shaping means such as an oscillating saw or hand saw is introduced into the guide surface to resect the femur. The device also includes stabilizing members with threaded knurled cap bolts with points that extend along the sides of the femur to stabilize the device.

Fargie, et al, U.S. Pat. No. 4,736,737 is a tibial cutting jig, having a base that interconnects with a intramedullary alignment rod installed along the axis of the tibia. The base includes outriggers carrying measurement keys for spacing the base a preselected distance above the tibia. A saw guide is attached to the base and is positioned to allow for cutting of the tibia at a selected position.

Whiteside, et al, U.S. Pat. No. 5,002,545 discloses a shaping guide for accurately shaping the tibial plateau comprising an alignment rod located anterior to the anterior cruciate ligament and along the anterior cortex of the intermedullary canal of the tibia. The shaping guide is interconnected with the rod and is adjustable with respect to the rod to control the amount of resection of the tibial plateau by raising or lowering the cutting guide surfaces. The device includes a pin which is inserted into a hole on the alignment guide for setting rotation alignment by aligning the pin with the intercondylar notch of the femur.

Poggie et al., U.S. Pat. No. 5,250,050 discloses an apparatus for use in a total knee prothesis comprising cutting guides, templates, alignment guides, a distractor and clamping instruments. The lateral anterior prominence is resected from the distal femur for preparing the distal femur for the distal femoral cutting block. A hole is first drilled in line with the medullary canal midway between the medial and lateral femoral condyles just anterior to the posterior cruciate. The right or left alignment fork is introduced into the medullary canal. The femoral distractor is slid onto the alignment fork and the leg extended. The distractor is keyed to the femur at the appropriate angle of valgus from the mechanical axis of the frontal plane and perpendicular to the sagittal plane. The femoral distractor sits flush on the cut proximal tibia. A lateral and medial arms of the distractor are distracted up to the femoral condyles with the knee in full extension. Ligamentous releases may be performed to balance the ligaments. The drill guide slides up to the anterior femur and two pins may be tapped through the holes to correspond to the tibial thickness. The drill guide slides off leaving the pins in place. The tension of the distractor may be released and the distractor removed. The knee is flexed to 90 degrees and the alignment fork is removed. The distal cutting guide slides onto the pins and an oscillating saw is used to resect the distal femoral condyles. The distractor is then inserted between the femur and tibia, and it is distracted. The drill guide is used to tap two pins into the resected femur. Then the drill guide is removed, tension released and the distractor removed. Then the AP sizer is slid onto the pins and the feelers engaged and the body is lowered and rotated until the feeler touches the high point of the anterior cortex. Then a chamfer block is engaged with the pins and femoral cuts may be made.

Stillwell, U.S. Pat. No. 4,457,307, which discloses a movable saw and saw carriage which may be mounted to a patient's femur and positioned to cut the femur bone. An elongated rail is secured substantially parallel to the femur. A saw carriage and a carriage housing are attached to the rail. The saw has a blade extending substantially parallel to the direction of linear movement of the saw carriage. The saw carriage is slidably guided along paths substantially parallel to the elongated rails for making cuts in the femur bone. The saw may be positioned in a plurality of second positions where the saw carriage is slidably guided in paths substantially perpendicular to the elongated rail for making traverse distal femur cuts and for scoring the tibia cortex. Additionally, the saw may be positioned in a plurality of third positions where the saw carriage is slidably guided to form an acute angle with the elongated rail for making anterior and posterior femur chamfer cuts.

Keller, U.S. Pat. No. 4,586,496, discloses a surgical chisel having a flexurally rigid chisel shank and a thin, elongated chisel blade fixed at its front end. A chisel guide is provided having slides for displaceably guiding the blade and shank in a longitudinal direction.

Zarnowski et al., U.S. Pat. No. 4,892,093, discloses a cutting guide for a saw blade for resecting a femur. The device is attached to a femur after the distal end has been removed and a transverse surface has been established. The cutting guide includes a base member having a planar base surface. A pair of laterally spaced-apart locating and securing posts are integral with the base member and project in a direction normal to the base surface to interconnect with the femur. Guide members in the form of cylindrical bars are positioned within side members attached to the base. A saw blade may be inserted between the guide surfaces to properly position the blade to cut the femur.

Vandewalls, U.S. Pat. No. 4,896,663, discloses a drill for drilling a hole into a femur. The device includes a positioning mechanism to firmly engage the outer peripheral surface of the femoral head and the femoral neck. This immobilizes the drill bushing relative to the femur and orients the axis of the drill with the central axis of the femur.

Schmidt, U.S. Pat. No. 5,049,149, discloses a sawing gauge system for intertrochantery accommodation osteotomies for removing a wedge-shaped section of bone with a predetermined wedge-angle so that an optimal pre-stress load F can act.

Lackey, U.S. Pat. No. 5,053,037, discloses a femoral drill guide with interchangeable femoral collets, a femoral reamer and a femoral anterior/posterior cutting block with an adoptable anterior femoral ledge. A plurality of diagonal slots are provided for making diagonal cuts in the distal end of the femur.

Ferrante et al. U.S. Pat. No. 5,098,436, discloses a modular guide for shaping a femur comprising a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove and a portion of the selected area exposed through the opening. A second bracket defines a linear slotted bore extending generally parallel to the long axis of the femur for guiding a second shaping tool to form a relatively deep recess accommodating an intercondylar-stabilizing housing of a knee implant.

Brown, U.S. Pat. No. 5,234,432, discloses a method of cutting the proximal end of a femur prior to cementing in a prosthesis for reconstructive hip surgery.

Additionally, Whiteside, U.S. Pat. No. 4,474,177 describes instruments for creating the distal femoral surfaces where a guide is used to index a flat surface used to guide the distal femoral resection. Kaufman, et al. U.S. Pat. No. 4,721,104 describes a method of preparing the intracondylar area of the distal femur. In addition, Kenna, U.S. Pat. No. 4,787,383 describes a saw and saw guide used to perform the most distal planar femoral resection. Jellicoe, U.S. Pat. No. 5,047,032 utilizes a side cutting drill to form the distal femoral surface.

These previous devices have not dealt with properly locating and orienting placement of a cutting guide on the distal femur, for resecting the femur, based on the orientation of the resected proximal tibia. These past efforts locate and orient cutting guides on the distal femur by "eye" or other, equally imprecise methods. Accordingly, none of these prior efforts, taken alone or in combination, teach or suggest the benefits of the present invention, nor the structure and method of the present invention for achieving these benefits.

OBJECTS AND SUMMARY OF THE INVENTION

It is a primary object of the present invention to provide an apparatus for properly resecting the distal human femur.

It is also an object of this invention to provide an apparatus for properly orienting the resections of the distal human femur.

It is also an object of the present invention to provide an alignment guide apparatus for properly orienting and locating some or all of the distal femoral resections necessary in human total knee arthroplasty.

It is an object of the alignment guide apparatus of the present invention to provide a means for directly or indirectly establishing the proper orientation cutting guide devices for performing distal femoral resections.

It is even an additional objective of the alignment guide apparatus of the present invention to provide a means for directly establishing the proper location of cutting guide devices used to perform distal femoral resections.

It is also an object of the present invention to provide an extension block for determining the gap between a resected proximal tibia and a resected or unresected distal-most surface of the human femur in extension and to allow for appropriate ligament balancing.

It is an additional object of the present invention to provide an extension block for adjusting and balancing the gap between a resected proximal tibia and an unresected or partially resected distal femur.

It is another object of the alignment guide apparatus to provide an alignment device which references the resected surface of the proximal tibia to indicate the proper location and orientation of the device(s) used to guide the cutting devices used to perform the distal femoral resections.

It is another object of this invention to provide an apparatus which is simple in the design and precise and accurate in operation.

These objects and others are met by the femoral resection alignment method and apparatus of the present invention. This apparatus comprises a number of components including a guide body component, an extension block component, a rotating arm component, an extension rod component, and a tibial referencing component. The guide body component contacts the distal-most surface of the femur. Its location is based off of the posterior femoral condyles and the surface of the distal-most femoral resection or the unresected distal-most femoral surface. The rotating arm component is interconnected with the guide body and may rotate with respect thereto, thus allowing for the direct or indirect adjustment of the rotating alignment of cutting guides for resecting the distal femur. In one embodiment, the rotating arm component carries arms with drill screw apertures which direct placement of drill holes in the femur which are used to attach a cutting guide to the femur. In another embodiment the rotating arm component extends above the femur and receives a femoral milling device as shown in U.S. patent application Ser. No. 08/300,379. The rotating arm component is attached to the extension rod component which extends to the tibial referencing component which references the location and orientation of the proximal resected surface of the tibia. Thus the rotating alignment of the distal femoral prosthesis is established with respect to the orientation of the resected proximal tibial surface.

The rotational alignment of the rotating arm component is approximately perpendicular the rotational alignment of the extension rod component in both Anterior/Posterior and Mediolateral planes. The extension rod component contains a means for adjusting the distance between the tibial referencing component and the rotating arm component. The rotating arm component is able to rotate with respect to the guide body which is firmly fixed to the distal femur. The extension rod is firmly fixed in the tibial referencing component which rests on the resected tibial surface. The adjustment of the distance between the tibial referencing component and the rotating arm component distracts the femur from the tibia until distraction is restricted by the collateral ligaments and other soft tissues present in the knee joint. Thus the location and orientation of the distal femoral prosthesis is properly determined with respect to the proximal tibial resection and the soft tissue of the knee joint.

The rotational alignment of the drill holes in the resected distal femur should be parallel to the resected proximal tibia when equal ligament tension is attained through the distraction of the femur from the tibia.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

Figure 1:
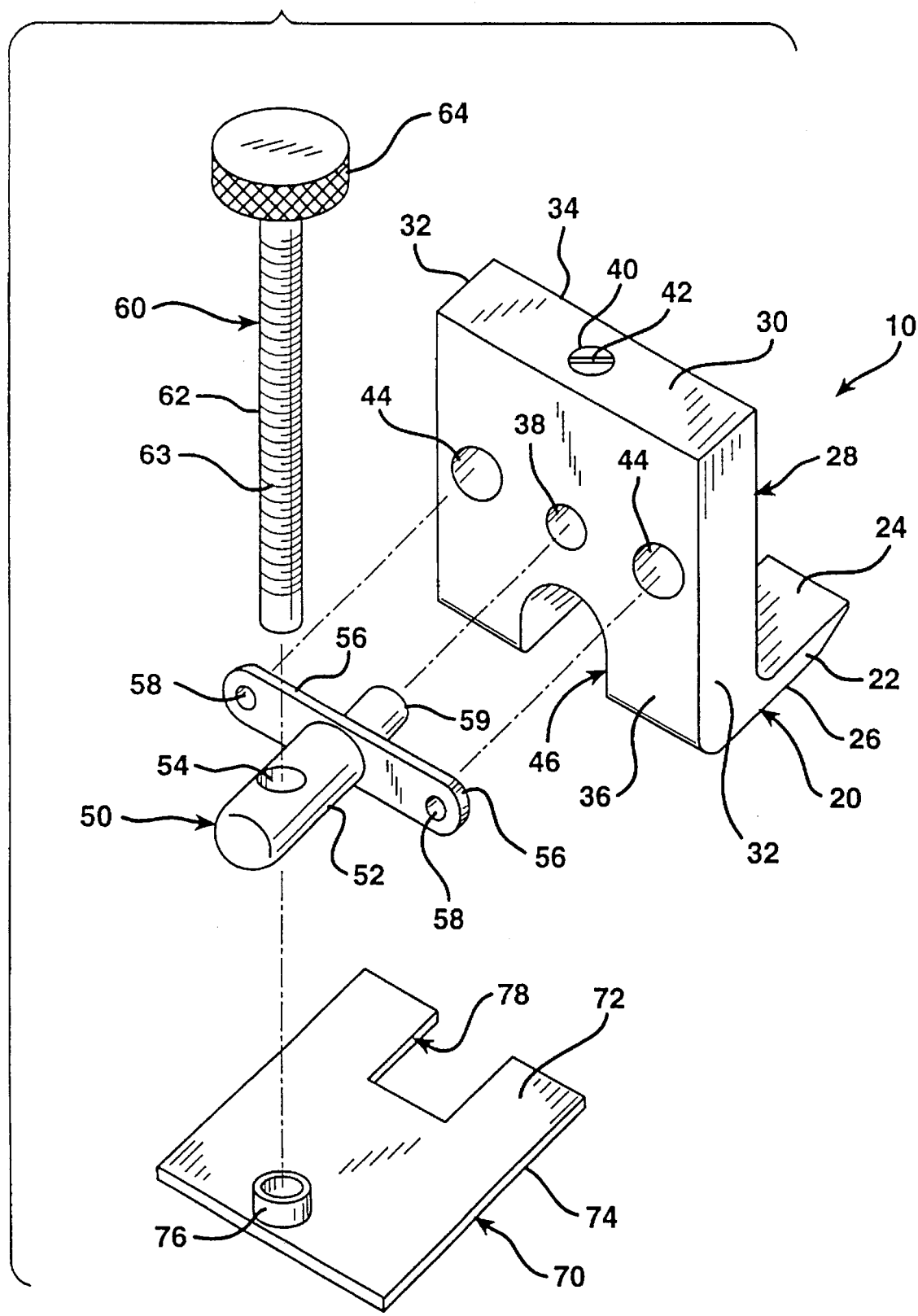
FIG. 1 is an exploded view of the femoral resection alignment apparatus of the present invention showing the guide body component, a rotating arm component, an extension rod component, and a tibial referencing component.
Figure 2:
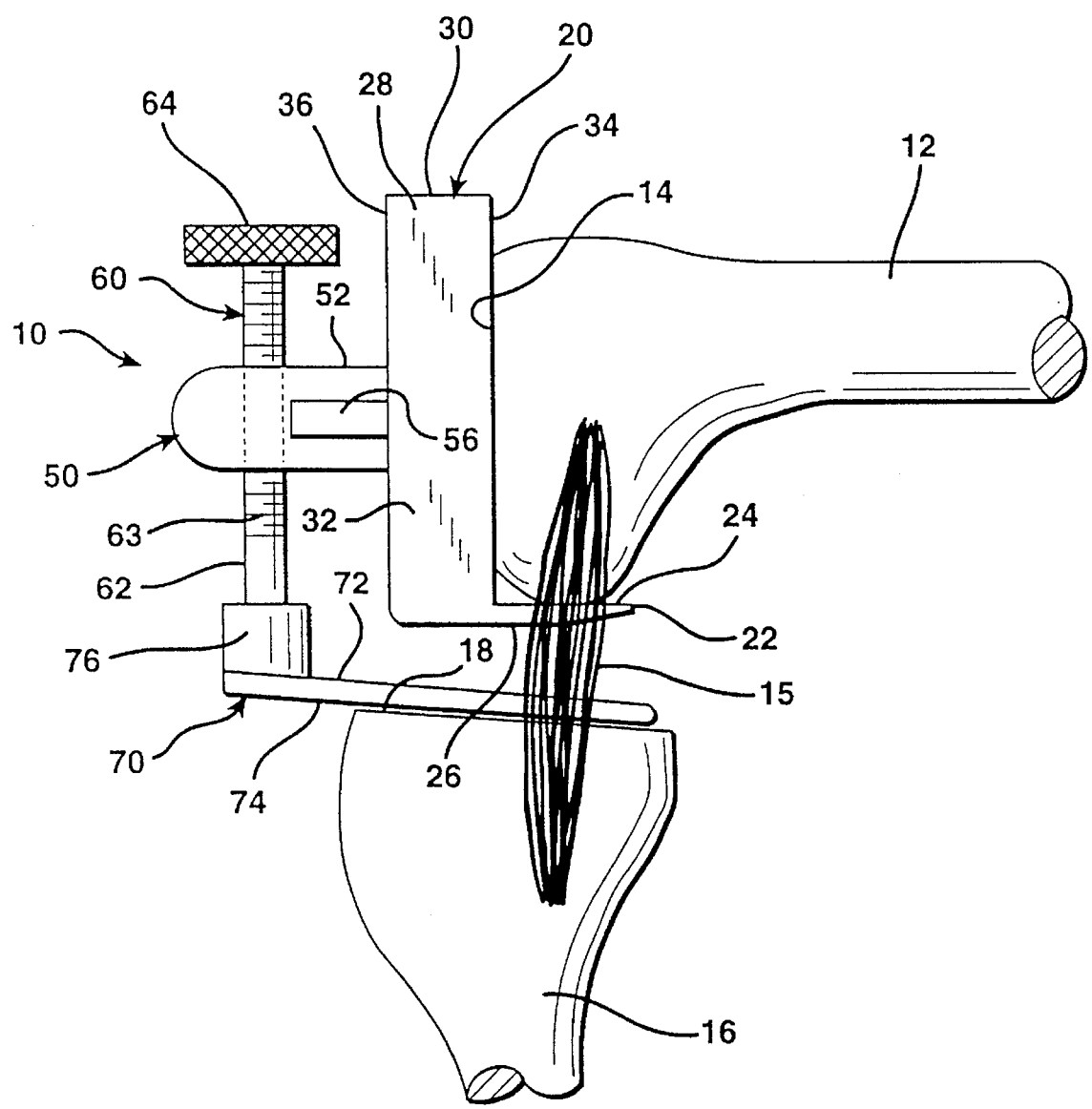
FIG. 2 is a side plan view of the apparatus shown in FIG. 1 attached to a flexed human knee joint including a distal femur, a resected proximal tibia, and collateral ligaments.
Figure 3:
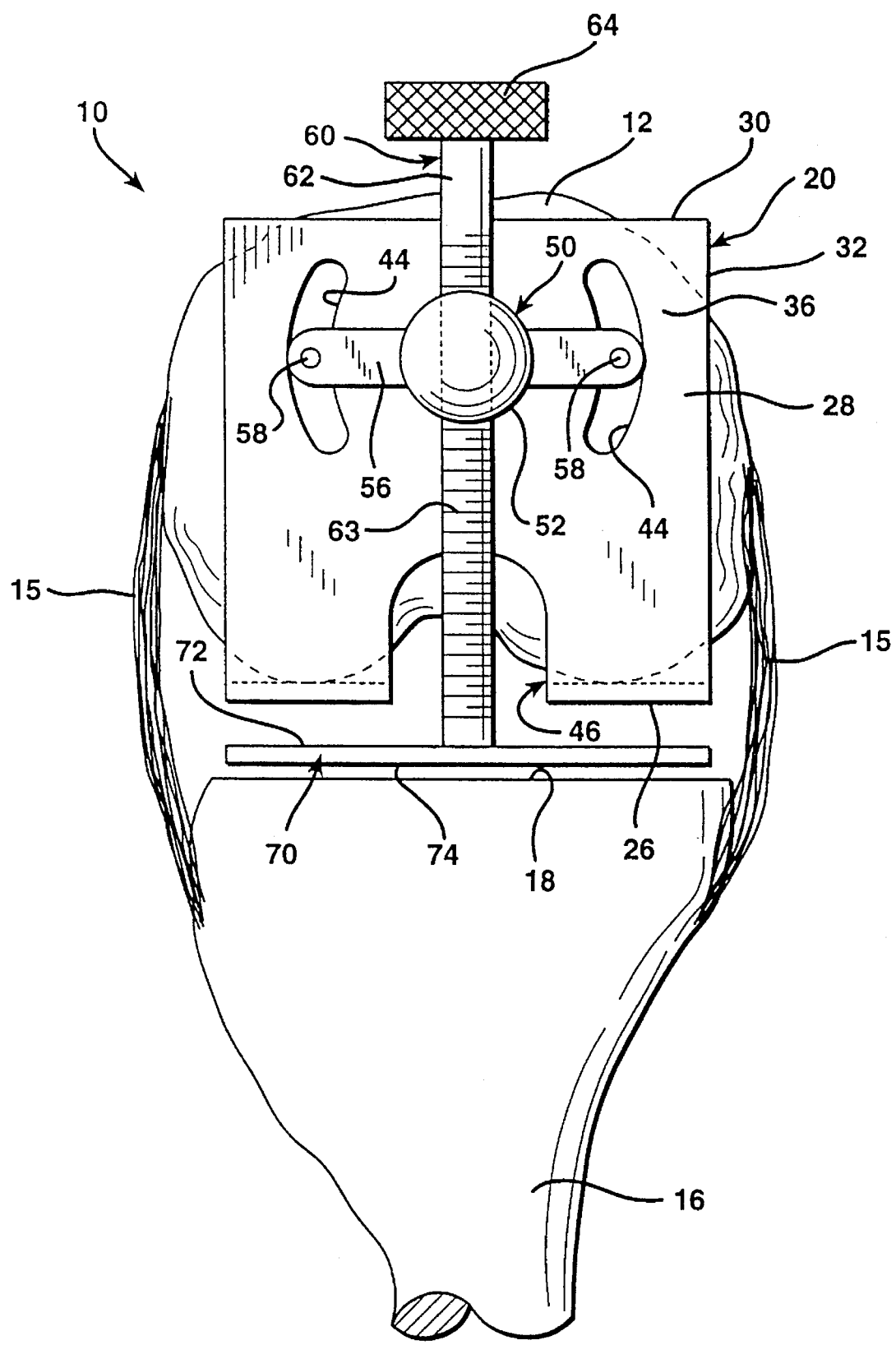
FIG. 3 is a front plan view of the apparatus shown in FIG. 1 attached to a flexed human knee joint including the distal femur, the partially resected proximal tibia, and the collateral ligaments.

Shown in FIGS. 1, 2 and 3 is the femoral resection alignment apparatus of the present invention, generally indicated at 10. The femoral resection alignment apparatus 10 includes a guide body component generally indicated at 20, a rotating arm component generally indicated at 50, an extension rod component generally indicated at 60, and a tibia referencing component generally indicated at 70. These components cooperate to properly locate and orient drill holes 80 on the distal femur for attaching a cutting guide device, not shown, for resecting the distal femur. As will be described, the cutting guide employed may be one conventionally known in the art or the one described in copending U.S. patent application Ser. No. 08/300,379, filed Sep. 2, 1994, the entire disclosure of which is incorporated herein by reference.

As shown in FIG. 1, the guide body component generally indicated at 20 includes a guide body generally indicated at 28 having tongues 22 extending from a lower end thereof. The tongues 22 include an upper surface 24 for contacting and distracting the distal femur with respect to the proximal tibia as hereinafter described. The tongues also include a lower surface 26.

The guide body 28 includes top surface 30, sides 32, front surface 34 and rear surface 36. Extending through the guide body 28 from the front 34 towards the rear 36 is rotating arm aperture 38. The rotating arm aperture 38 is positioned generally in the center of guide body 28, and accepts the rotating arm component as hereinafter described. A rotating arm lock aperture 40 extends from the top 30 of the guide body 28 to the rotating arm aperture 38 and rotating arm lock screw 42 is threadibly engagable therewith. The rotating arm lock screw 42 may be turned down through the guide body 28 to contact the rotating arm component 50 and lock the rotating arm component 50 into a desired position.

Flanking the rotating arm aperture 38 are drill hole apertures 44 which may be any desired shape and which extend through guide body 28 from the front 34 to the rear 36. The guide body 28 also includes a body spacing aperture 46 extending into the guide body 28 from a lower end thereof, and positioned central to the width of the guide body 28, typically between the parallel tongues 24. The spacing aperture 46 prevents interference between the guide body 28 and posterior cruciate ligament and/or the tibia eminence during use.

Rotating arm component, generally indicated at 50, includes a cylindrical body 52 having an extension rod aperture 54 extending therethrough to receive extension rod component generally indicated at 60. Extending outwardly from the cylindrical body 52 of rotating arm component 50 are arms 56 having drill screw apertures 58 positioned at outer ends thereof. Additionally, extending from the cylindrical body 52 is arm attachment shaft 59 which is sized to be received in the rotating arm aperture 38 in guide body 28. Arm attachment shaft 59 may be rotated within rotating arm aperture 38 of guide body 28 and when in a desired position, can be locked into such position by tightening down rotating arm lock screw 42 to contact the arm attachment shaft 59 within the rotating arm aperture 38 of guide body 28.

An extension rod component, generally indicated at 60, includes a rod shaft 62 having threads 63 formed thereon. The extension rod component 60 also includes a rod handle 64 at an upper end of the rod shaft 62. The rod shaft 62 extends through the extension rod aperture 54 in rotating arm component 50 and is threadibly engaged therewith. Rotation of the extension rod component 60 by rotating the rod handle 64 causes the rotating arm component 50 to travel up or down the rod shaft 62 in accordance with the direction of rotation of the extension rod component 60.

The tibia referencing component, generally indicated at 70, includes an upper surface 72, a lower surface 74, an extension rod attachment means 76 and a spacing channel 78. The tibia referencing component 70 is interconnected with the extension rod component 60 by receiving a lower end of the rod shaft 62, opposite the rod handle 64, in the extension rod attachment means 76. Preferably, the extension rod attachment means 76 interconnects the rod shaft 62 with the tibia referencing component 70 and permits the rod shaft 62 to be freely rotated therein.

As seen in FIG. 2, in its operative position, the femoral resection alignment device 10 is positioned within the knee joint in flexion between the resected surface 18 of tibia 16 and the resected surface 14 of the femur 12. The lower surface 74 of the tibia referencing component 70 contacts the resected proximal surface 18 of the tibia 16. The extension rod component 60 extends up from the tibia referencing component 70, the rod shaft 62 interconnected with the extension rod attachment means 76 which holds the rod shaft 62 perpendicular to the tibia referencing component 70. Riding on the rod shaft 62 is rotating arm component 50.

The arm attachment shaft 59 of the rotating arm component 50 is received by the guide body 28 through the rotating arm aperture 38, as shown in FIG. 1. The front 34 of the guide body 28 contacts the resected surface 14 of the femur 12 and is firmly attached thereto. The tongues 22 extending from the guide body 28 are positioned below the posterior condyles of the femur 12 and the upper surfaces 24 of the tongues 22 contact the posterior condyles of the femur 12.

In operation, the tibia referencing component 70 contacts the resected proximal surface 18 of the tibia 16 and the extension rod component 60 is actuated to lift the rotating arm component 50 and accordingly, the guide body 28 and the tongues 22 to distract the femur 12 with respect to the tibia 16. The collateral ligaments 15 are accordingly drawn up to a tensioned position.

As best shown in FIG. 3, after the femur 12 is distracted with respect to the tibia 16, it can be seen that the arms 56 extending from the rotating arm component 50 are positioned parallel to the tibia referencing component 70. Thus, an imaginary line extending through drill screw apertures 58 in arms 56 is parallel to the tibia referencing component 70. After the femur is properly distracted from the tibia, the rotating arm component 50 may be fixed with respect to the guide body 28 by screwing the rotating arm lock screw 42 against the arm attachment shaft 59 of the rotating arm component 50, as shown in FIG. 1a. Thereafter, any conventional drill may be extended through the drill screw apertures 58 in arms 56 to drill holes into the distal femur 12. Accordingly, an imaginary line through the drill holes in the distal femur 12 are parallel to the tibia referencing component 70 and hence to the resected surface 18 of the tibia 16. Thereafter, the femoral resection apparatus 10 can be removed from its position.

Figure 4:
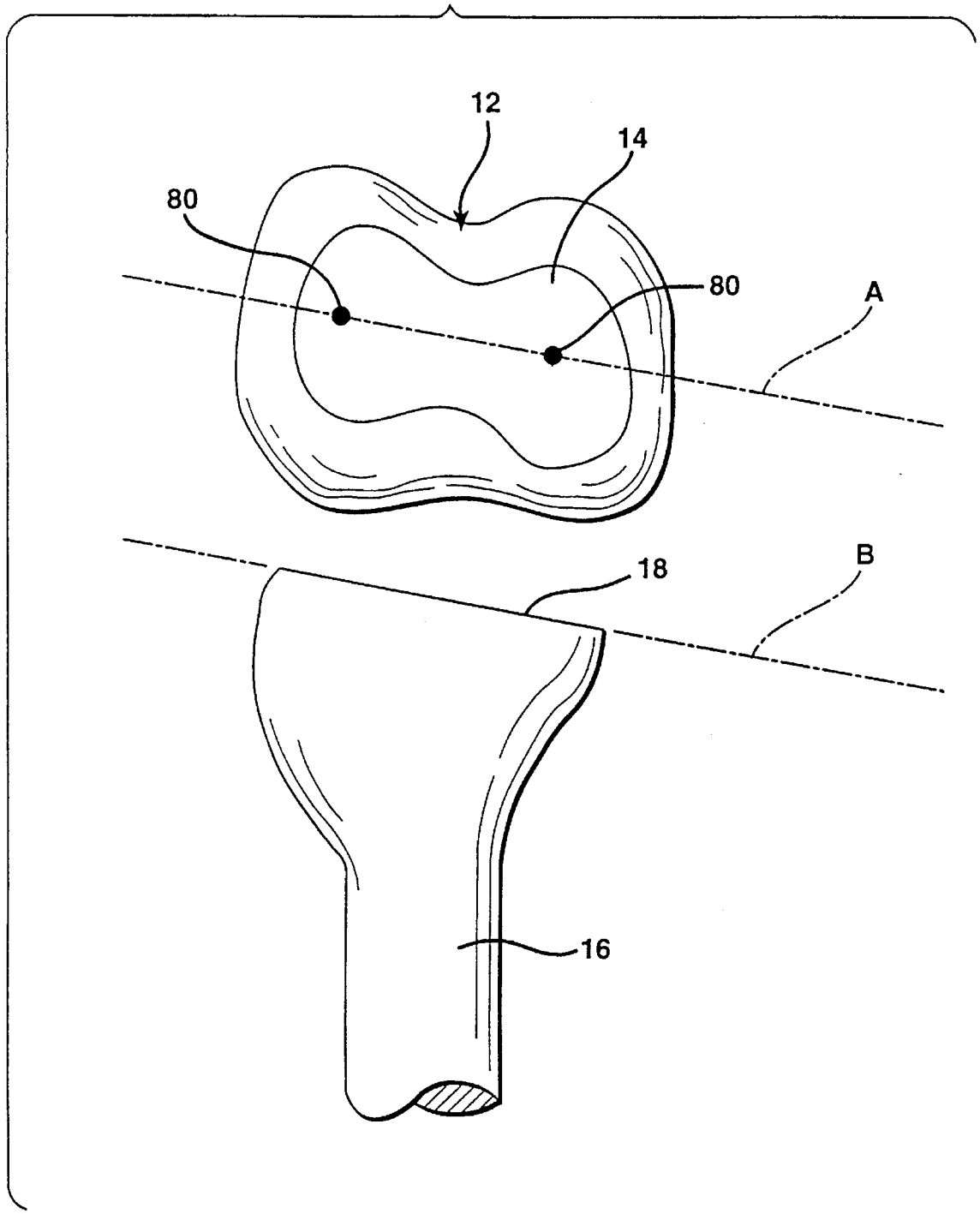
FIG. 4 is an exaggerated front plan view of a partially resected distal femur and a resected proximal tibia after use of the apparatus of the present invention shown in FIG. 1 showing placement of drill holes for attaching a cutting guide to allow for indirect control of the orientation and location of a conventional cutting guide.

As shown in FIG. 4, the drill holes 80 in the femur 12 are positioned along an imaginary line A. Imaginary line A is parallel to imaginary line B that extends along the resected surface 18 of the tibia 16. Accordingly, the drill holes 80 in the femur 12 are properly oriented based on the orientation of the resected surface 18 of the tibia 16. Additionally, because the femoral resection alignment device has been used to distract the femur 12 with respect to the tibia 16, the drill holes 80 are properly located on the femur.

Thereafter, a conventional cutting guide device, not shown, can be attached to the femur using drill holes 80 for receiving attachment means to attach the cutting guide device at a proper location and orientation of the femur. Then, means for resecting the femur, as known in the art, can be used to resection the femur. Because the drill holes 80 are properly located and oriented on the femur, and thus the cutting guide device is also properly located and oriented, the resected femur surfaces will likewise be properly located and oriented.

Figure 5:
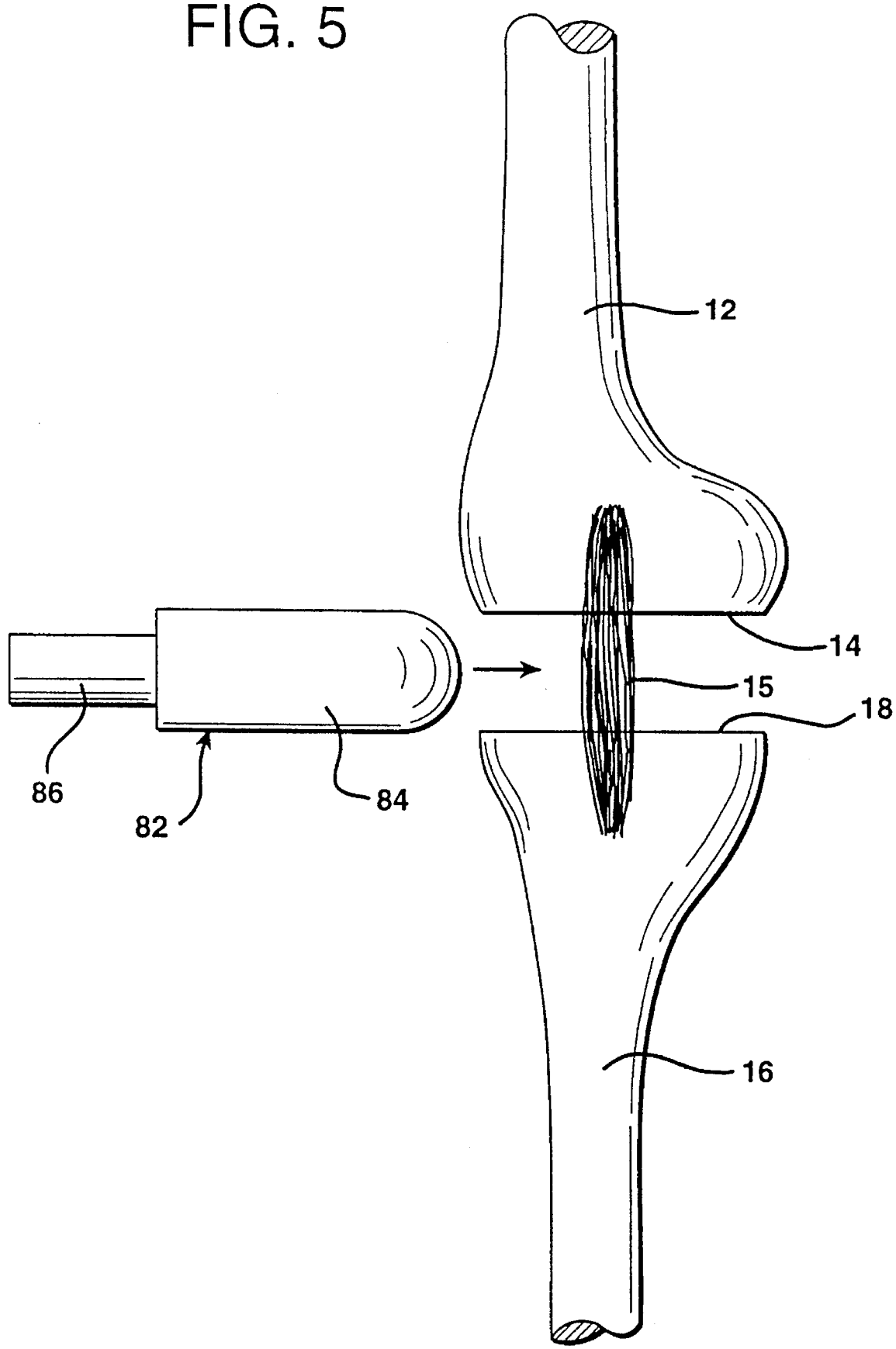
FIG. 5 is a side plan view of the extension block component of the present invention for placement between the partially resected distal femur and the resected proximal tibia by use of the apparatus of FIG. 1.
Figure 6:
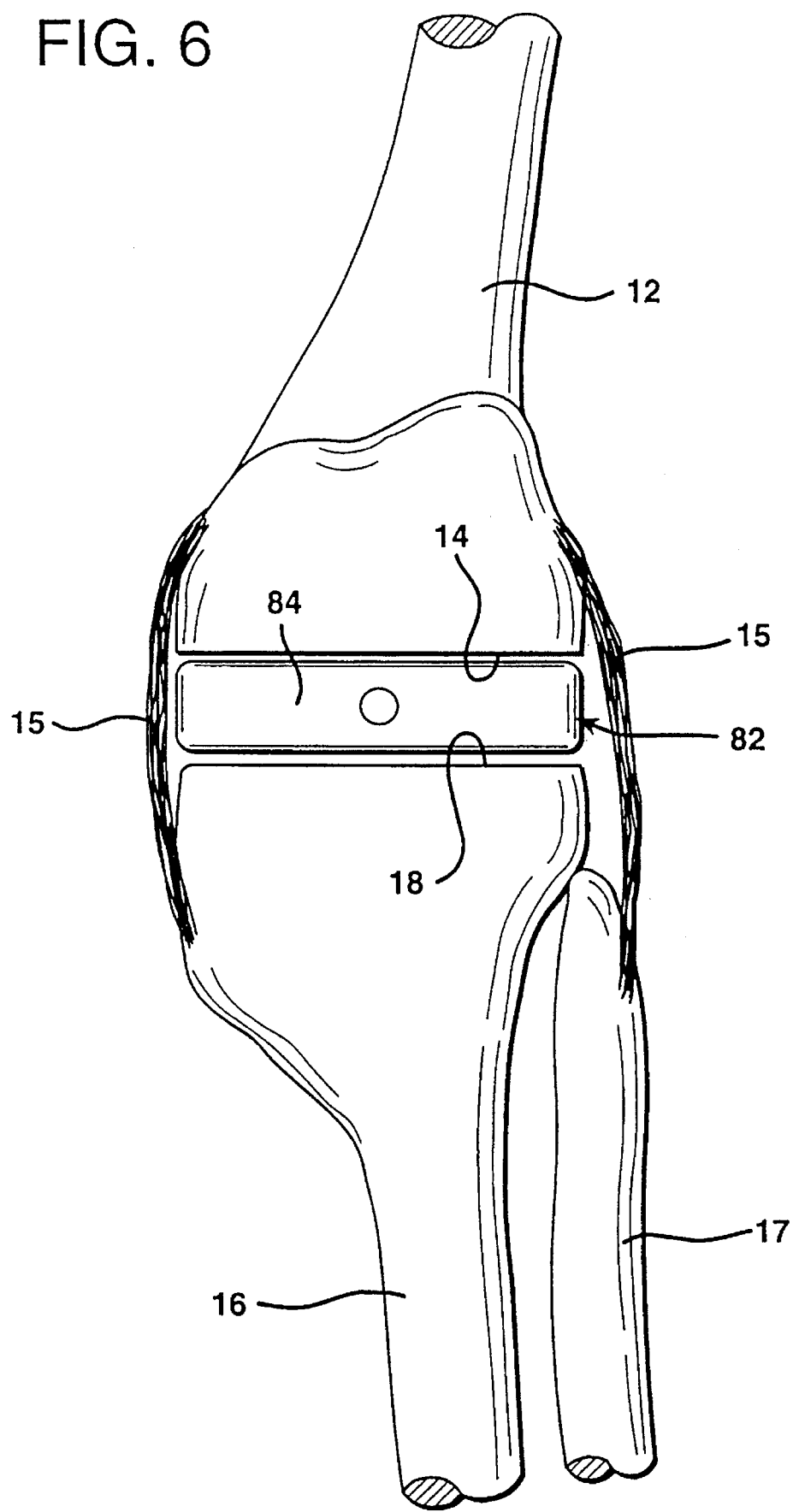
FIG. 6 is a front plan view of the extension block shown in FIG. 5 placed between the partially resected distal femur and the resected proximal tibia by use of the apparatus of FIG. 1.

As shown in FIG. 5 and 6, the extension block component, generally indicated at 82, includes an extension block body 84 and handle 86. Prior to utilizing the femoral resection alignment device to properly locate and orient the drill holes in the femur, the leg is put into extension and the extension block component 82 is inserted between the resected surfaces 14 and 18 of the femur 12 and tibia 16 respectively. The extension block body 84 comes in various sizes. A typical block may be seventeen millimeters thick. The extension block component 82, when in place between the tibia and femur, facilitates ligamentous release of collateral ligaments 15 extending between the femur 12 and tibia 16 on one side and the femur 12 and fibula 17 on the other side to provide even tension on both sides of the knee joint.

The method of using the femoral resection alignment apparatus of the present invention comprises the steps of: resecting the proximal tibia; moving the leg into extension; inserting the extension block component between the resected proximal tibia and the femur (which may or may not be partially resected); performing ligamentous release of collateral ligaments to provide even tension of the collateral ligaments on both sides of the knee joint; placing the leg into flexion; contacting the lower surface of the tibia referencing component against the resected tibia; contacting the upper surface of the tongue of the guide body against the posterior condyles of the femur; distracting the femur from the tibia by actuating the rod shaft of the extension rod component to move the rotating arm component and hence the guide body vertically away from the tibia until the collateral ligaments are tensioned; fixedly attaching the guide body to the femur; drilling drill holes into the femur through drill screw apertures in the arms of the rotating arm component; removing the femoral resection alignment apparatus; and attaching a cutting guide device to the femur through the drill holes.

The femoral resection alignment method and apparatus is intended to work with a conventional femur resection system by ensuring that the drill holes that are placed on the face of the distal femoral resection are parallel to the proximal tibial resection when the collateral ligaments are balanced. Since the drill holes dictate the location and orientation of the cutting blocks, this device ensures that the rotating alignment of the distal femoral resections and therefore, the rotating alignment of the distal femoral prosthesis, is the same as the proximal tibial resection when the collateral ligaments are "balanced" (under equal tension).

Figure 7:
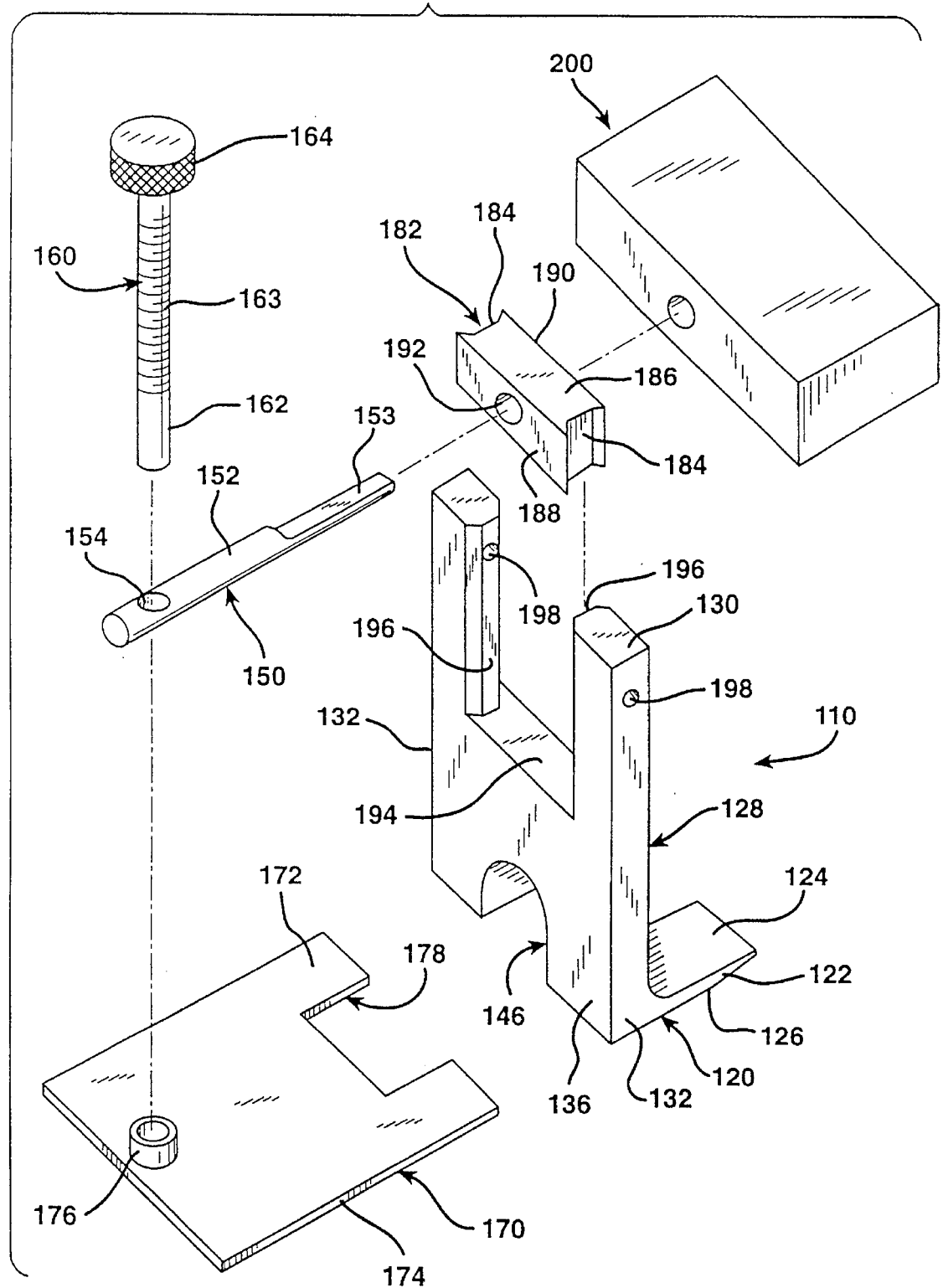
FIG. 7 is an exploded view of another embodiment of the femoral alignment apparatus of the present invention showing the guide body component, a rotating arm component, an extension rod component, and a tibial referencing component.
Figure 8:
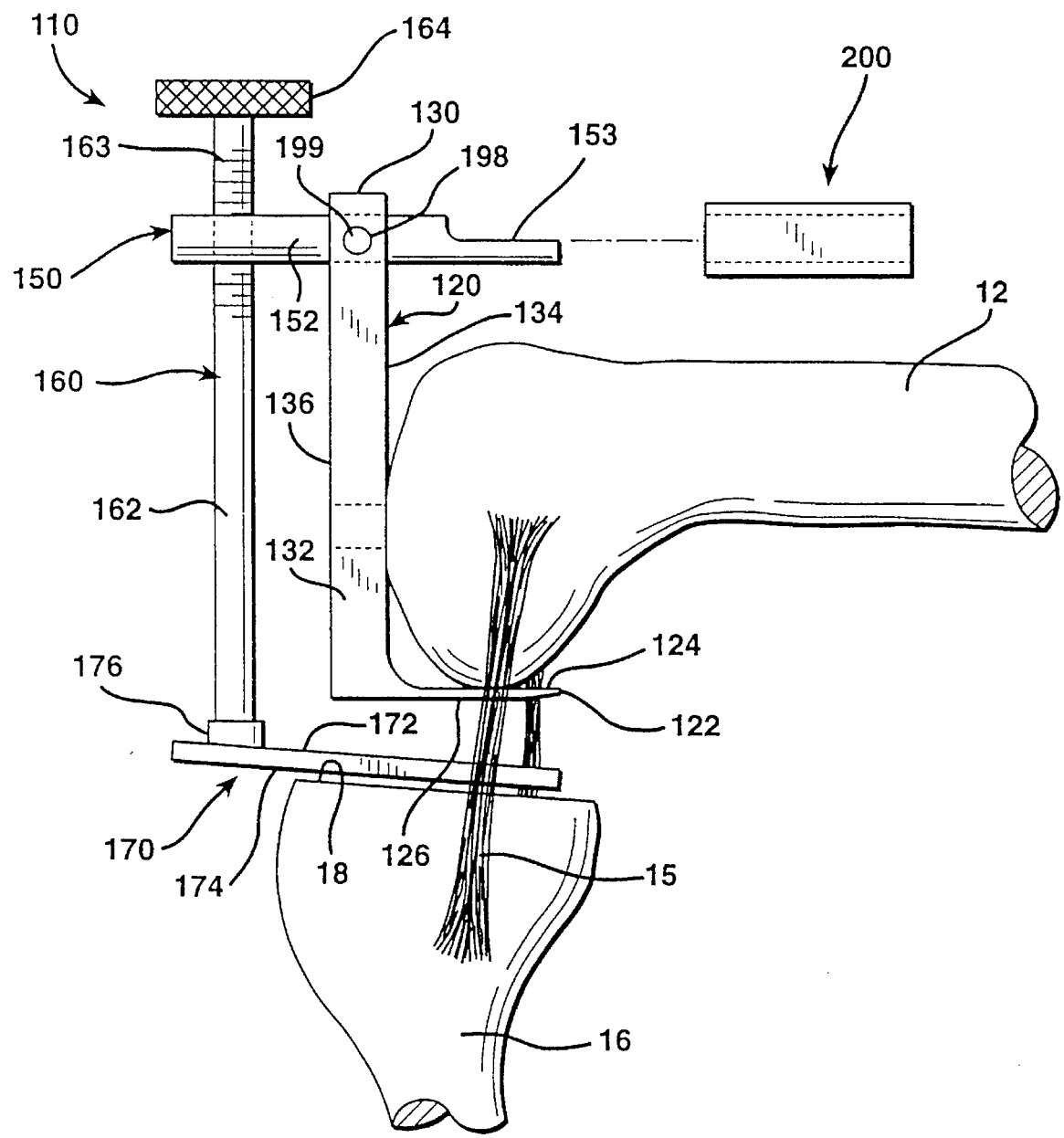
FIG. 8 is a side plan view of the apparatus shown in FIG. 7 attached to a flexed human knee joint including a distal femur, a partially resected proximal tibia and collateral ligaments.
Figure 9:
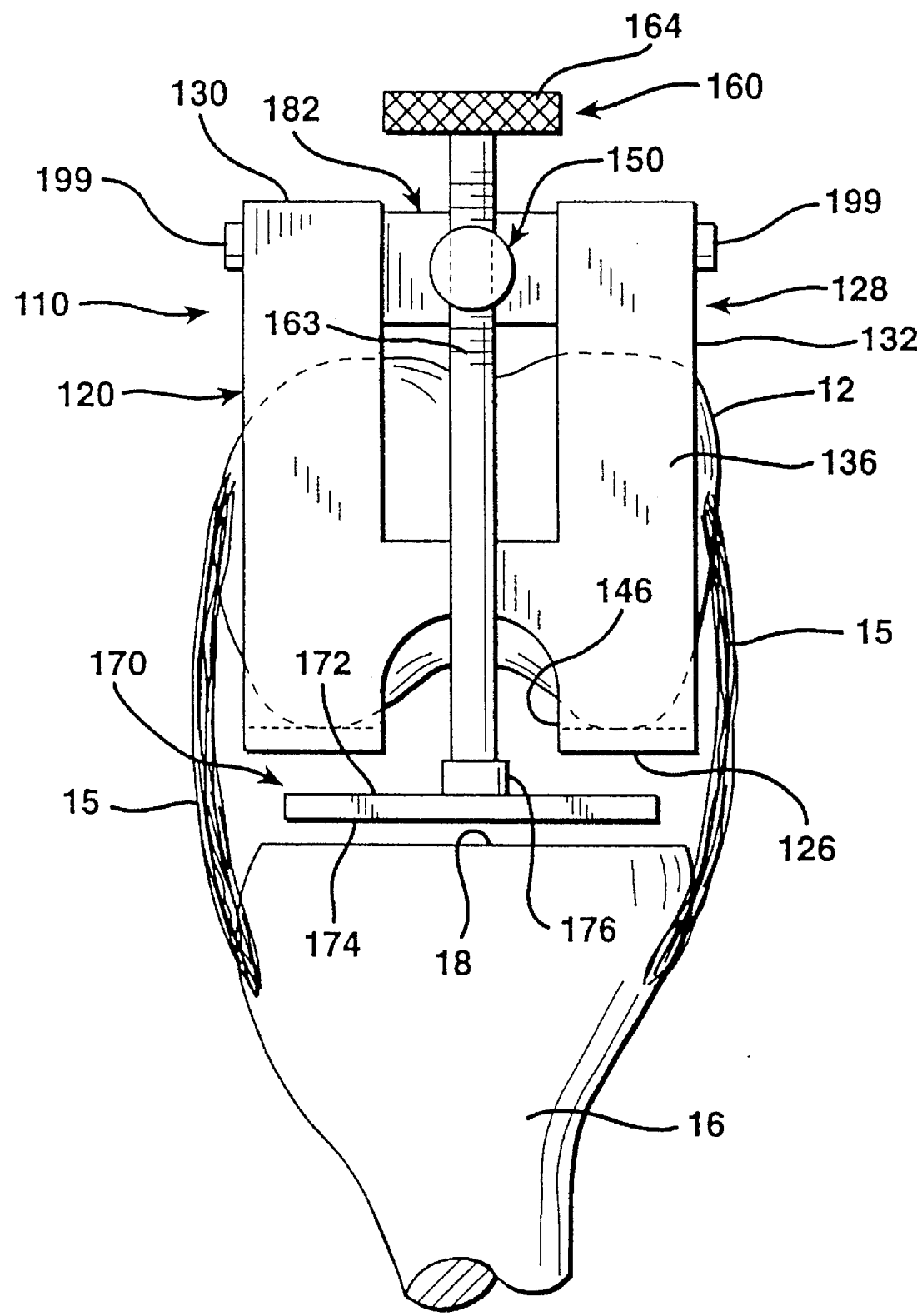
FIG. 9 is a front plan view of the apparatus shown in FIG. 7 attached to a flexed human knee joint including the distal femur, the partially resected proximal tibia, and the collateral ligaments.

In another embodiment of the present invention, as shown in FIGS. 7–9, the femoral resection alignment apparatus is adapted to work in conjunction with a system like the Femoral Resection apparatus described in U.S. patent application Ser. No. 08/300,379 filed Sep. 2, 1994 which includes a pattern means positioned about the femur for guiding the resecting of the femur. Use of the present alignment device with Femoral Resection Apparatus permits the location and orientation of the pattern means to be directly controlled through the rotating arm component. In the configuration described in the previous patent application, the shaft of the rotating arm component terminates in the block that allows it to be fastened to the femoral alignment positioning body.

Referring now to FIGS. 7–9, wherein corresponding elements of FIGS. 1–3 are indicated with corresponding reference numerals with the addition of 100. The shaft 152 of the rotating arm component 150 extends through the block 182 and is free to rotate in the block 182. One end 153 of the rotating arm component 150 mates with the crossbar 200 and dictates the rotational alignment thereof, while the other end mates with the extension rod 160 of the present invention. Since the extension rod 160 is connected to tibial referencing plate 170, the rotating angle of crossbar 200 and thereby the pattern device that may be attached thereto, not shown, is based off of the proximal tibial resection.

More specifically, the apparatus shown in FIGS. 7–9 is generally indicated at 110 and includes a guide body 120, a rotating arm component 150, an extension rod component 160, and a tibia referencing component 170. These components cooperate to properly locate and orient a cross bar 200 for positioning a pattern device about the distal femur for resecting the distal femur for guiding cutting means for resecting the distal femur.

The guide body, generally indicated at 120, includes a body 128 having tongues 122 extending from a lower end thereof. The tongues 122 include an upper surface 124 for contacting and distracting the distal femur with respect to the proximal tibia. The tongues also include a lower surface 126.

The guide body 128 includes top surface 130, sides 132, front surface 134 and rear surface 136. The guide body further includes a channel extending into the body into the body 128 from the top surface 130. The channel is defined by side walls 196 and bottom wall 194 in guide body 128. The channel is sized to receive block 182 through which the rotating arm component 150 extends. The block 182 is vertically moveable within the channel of the guide body 128 and may be fixed into a desired position by lock screws 199 which extend through apertures 198 of the guide body 122 to contact side walls 184 of the block 182 to lock the block 182 within the channel. Positioning of the block 182 within the channel of the guide body 128 may be referenced by a numbered scale on the guide 128.

The rotating arm component 150 includes a shaft 152, a keyed surface 153 for attachment to cross bar 200 and an aperture 154 for receiving an extension rod therethrough. A shaft 152 extends through aperture 192 in block 182 and can rotate with respect thereto.

The extension rod component, generally indicated at 160, includes a rod shaft 162 having threads 163 formed thereon. Extension rod 160 also includes a rod handle 164 at an upper end of the rod shaft 162. The rod shaft 162 extends through the aperture 154 in the rotating arm component 150 and is threadibly engaged therewith. Rotation of the extension rod component 160 by rotating the rod handle 164 causes the rotating arm component 150 to travel up or down the rod shaft 162 in accordance with the direction of the rotation of the extension rod component 160. This causes the block 182 to move vertically with respect to the rod shaft 162 and in turn causes the guide body 120 to move up and down with respect to the extension rod 160.

The tibia referencing component, generally indicated at 170, includes an upper surface 172, a lower surface 174, an extension rod attachment means 176 and a spacing channel 178. The tibia referencing component 170 is interconnected with the extension rod component rod 160 by attachment means 176. Preferably, the extension rod attachment means 176 interconnects the tibia referencing component 170 with the rod shaft 162 and permits the rod shaft to be freely rotated therein.

As seen in its operative position in FIG. 8, the femoral resection alignment device 110 is positioned within the knee joint in flexion between resected surface 18 of the tibia 16 and the femur 12. The lower surface 174 of the tibia referencing component 170 contacts the resected proximal surface 18 of the tibia 16. The extension rod component 160 stands up from the tibia referencing component 170, the rod shaft 162 interconnected with the extension rod attachment means 176 which holds the rod shaft 162 perpendicular to the tibia referencing component 170. Riding on the rod shaft 162 is rotating arm component 150. The body 152 of the rotating arm component 150 is received by block 182 which is locked into position within the guide body 128 by locking screws 199 interconnected with the guide body 120. The tongues 122 of the guide body 128 are positioned below the posterior condyles of the femur 12 and the upper surfaces 124 of the tongues 122 contact the posterior condyles of the femur.

In operation, the tibia referencing component contacts the resected proximal surface 18 of the tibia 16 and the extension rod component 160 is actuated to lift the rotating arm component 150 and accordingly, the guide body 128 and tongues 122 to distract the femur 12 with respect to the tibia 16. The collateral ligaments 15 are accordingly drawn up to a tensioned position.

Figure 10:
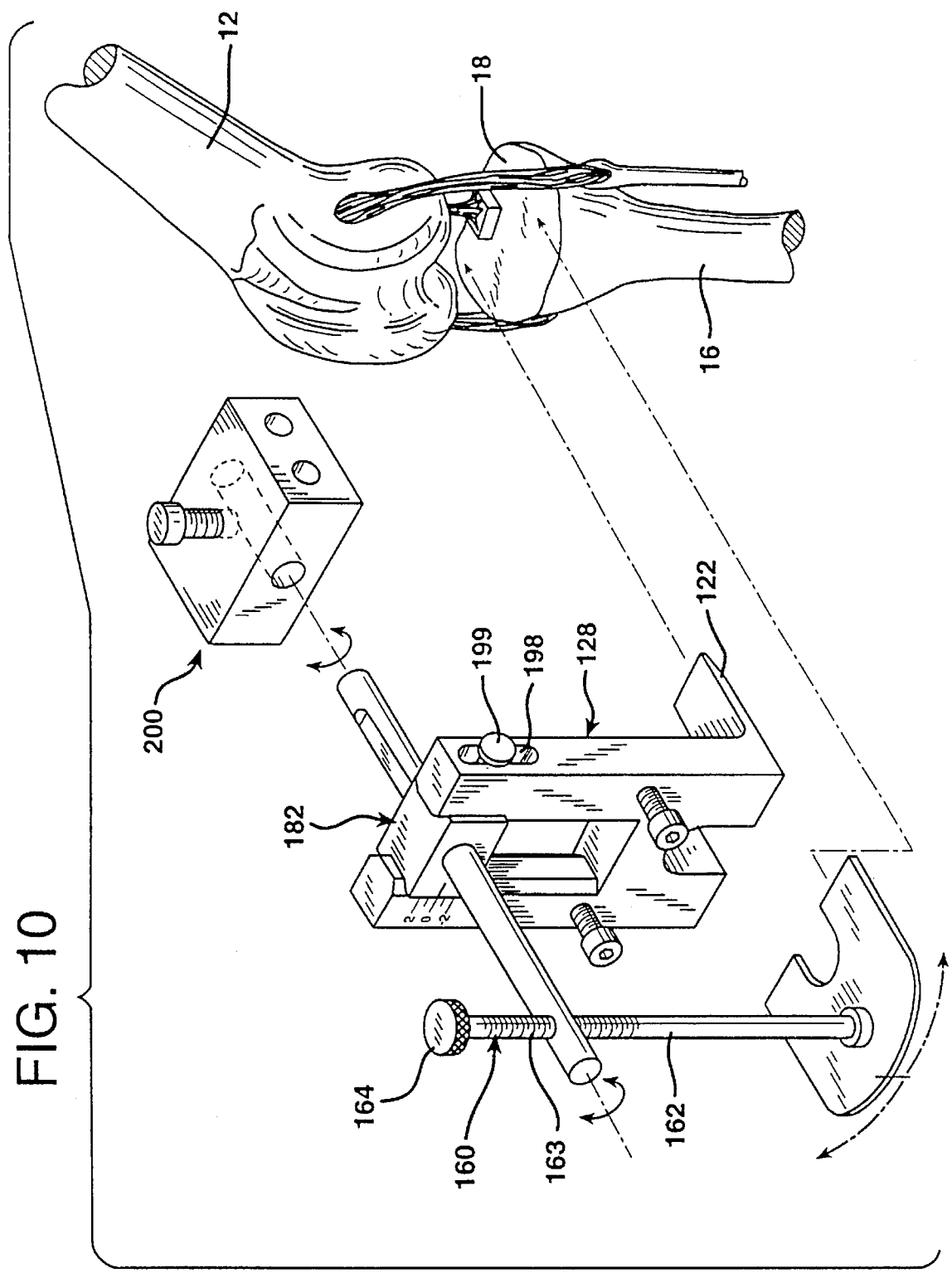
FIG. 10 is a partially exploded perspective view of the apparatus shown in FIG. 7.

As best shown in FIG. 9, after the femur 12 is distracted with respect to the tibia 16, it can be seen that the rotating arm component 150 rotates with the tibia referencing component 160. Thereafter, as can be seen in FIG. 10, after the femur is distracted from the tibia and the tibia referencing component 170 is placed on the resected tibia 16, the rotating arm component 150 is naturally rotated to correspond to the pitch of the resected tibia. Thereafter, the crossbar 200 can be placed onto the keyed surface 153 of the rotating arm component 150 to track the rotational alignment of the rotating arm component 150 to properly rotate the crossbar 200 with respect to the resected tibia 16. Thereafter, cutting guide devices, not shown, can be interconnected with the cross bar 200 to extend along the sides of the femur. The cutting guides are thereby accurately positioned for to guide a cutting means resecting the distal femur.

Also as shown in FIG. 10, the block 182 may have lock screws 199 attached thereto which extend through elongated apertures or slots 198 in the guide body 128 to permit adjusting the block 182 in the channel of the guide body 128 and then locking the position thereof. This allows for adjustment and fixation of the anterior-posterior positioning of the pattern device, and for the posterior resection to always parallel the proximal tibia cut.

Importantly, it is the overriding object of both embodiments of the present invention to provide a method and apparatus for locating and orienting the resections of the distal femur based on the resected surface of the proximal tibia. In both cases, this is achieved by putting the knee joint into flexion and distracting the femur with respect to the tibia to tension the collateral ligaments which have already been properly sized by means of ligamentous release. Thereafter, a cutting guide device, be it a conventional cutting guide device or the cutting guide device comprising the pattern device of Applicant's previous patent, is oriented with respect to the orientation of the resected proximal tibia. Other devices to accomplish this purpose are considered within the scope of the present invention.

With the proper use of the previously described system, extremely accurate and reproducible alignment and location of bone cuts are attainable. The preparation of femoral surfaces may be completed in any manner known in the art before and after using the instrumentation of the present invention.

Modifications of the foregoing may be made without departing from the spirit and scope of the invention. What is desired to be protected by Letters Patents is set forth in the appended claims.

What is claimed is:

1. An apparatus for locating and orienting a cutting guide for resecting a human distal femur comprising:

tibia referencing means for referencing a resected surface of a tibia;

extension means extending from the tibia referencing means;

rotational alignment means engageable with the extension means and movable therealong, the rotational alignment means including guide means for locating and orienting drill holes on a distal femur; and body means for contacting a distal femur, the body means including a tongue extending from a lower end thereof for contacting posterior condyles of a femur, the body means rotatably interconnected with the rotational alignment means.

2. The apparatus of claim 1 wherein the body means includes a lock aperture and lock means for locking the rotational alignment means with respect to the body means.

3. The apparatus of claim 1 wherein the body means includes drill apertures positioned in registration with the guide means of the rotational alignment means.

4. The apparatus of claim 3 further comprising drill means for extending through the guide means and the drill apertures for forming drill holes in a distal femur.

5. The apparatus of claim 3 wherein the drill apertures of the body means comprise elongated slots for registration with the guide means.

6. The apparatus of claim 1 wherein the rotational alignment means is maintained parallel to the tibia referencing means.

7. The apparatus of claim 1 wherein the extension means maintains the rotational alignment means parallel to the tibia referencing means.

8. The apparatus of claim 1 wherein the rotational alignment means includes arms for supporting the guide means.

9. The apparatus of claim 8 wherein the arms are fixed parallel to the tibia referencing means.

10. An apparatus for locating and orienting a cutting guide for resecting a human distal femur comprising:

a body including a front surface for contacting a human femur;

a tongue extending from a lower end of the body for extending under a human femur;

rotational alignment means interconnected with the body for rotating with respect to the body;

guide means positioned on the rotational alignment means for locating and orienting drill holes on a distal femur;

tibia referencing means for referencing a resected proximal tibia;

the tibia referencing means interconnected with the rotational alignment means by extension rod means.

11. The apparatus of claim 10 wherein the tongue includes two planar members positioned alongside each other with a space therebetween for accepting a posterior cruciate ligament.

12. The apparatus of claim 11 wherein the tibia referencing means includes a channel for accepting a posterior cruciate ligament.

13. The apparatus of claim 10 wherein the body includes drill apertures positioned in registration with the guide means of the rotational alignment means.

14. The apparatus of claim 13 further comprising drill means for extending through the guide means and the drill apertures for forming drill holes in a distal femur.

15. The apparatus of claim 10 wherein the rotational alignment means is maintained parallel to the tibia referencing means.

16. The apparatus of claim 15 wherein the rotational alignment means is movable along the extension rod means.

17. The apparatus of claim 10 wherein the rotational alignment means includes arms for supporting the guide means.

18. The apparatus of claim 17 wherein the arms are fixed parallel to the tibia referencing means.

19. An alignment apparatus for locating and orienting a cutting guide for resecting a human distal femur comprising:

a body including a front surface for contacting a human femur;

a tongue extending from a lower end of the body for extending under a human femur;

rotational alignment means rotatably interconnected with the body;

guide means interconnected with the rotational alignment means for locating and orienting drill holes on a distal femur;

tibia referencing means for referencing a resected proximal tibia;

extension means attached between the tibia referencing means and the rotational alignment means;

means for distracting the femur from the tibia by actuating the extension means to move the rotational alignment means and the body from the tibia referencing means.

20. The apparatus of claim 19 wherein the rotational alignment means is threadibly engaged with the extension means.

21. The apparatus of claim 20 wherein the extension means includes a handle at an upper end thereof and rotation of the handle moves the rotational alignment means along the extension means.

22. The apparatus of claim 21 wherein the rotational alignment means includes arms carrying the guide means.

23. The apparatus of claim 22 wherein the body includes drill apertures positioned in registration with the guide means of the rotational alignment means.

24. The apparatus of claim 23 further comprising drill means for extending through the guide means and the drill apertures for forming drill holes in a distal femur.

25. The apparatus of claim 24 wherein the arms are fixed parallel to the tibia referencing means.

26. A method for locating and orienting a cutting guide for resecting a human distal femur comprising the steps of:

contacting a tibia referencing component against a resected tibia;

contacting a body against distal femoral condyles of a human femur;

contacting a tongue extending from a lower end of the body against posterior femoral condyles;

distracting the femur from the tibia by actuating an extension rod extending between the tibia referencing component and the body;

drilling drill holes into the femur through drill hole apertures provided in arms of a rotational alignment component interconnected between the extension rod and the body;

removing the body from the femur;

attaching a cutting guide device to the femur through the drill holes.

27. The method of claim 26 further comprising, prior to contacting the tibia referencing component against a resected tibia, the steps of:

resecting the proximal tibia;

inserting an extension block component between the resected proximal tibia and the femur;

performing ligamentous release of collateral ligaments to provide even tension of the collateral ligaments.

28. The method of claim 27 wherein the step of distracting the femur with respect to the tibia comprises actuating the extension rod to move the rotational alignment component and the body with respect to the tibia referencing component.

29. The method of claim 28 wherein the rotational alignment component is threadibly engaged with the extension rod and rotating the extension rod moves the rotational alignment component and the body with respect to the tibia referencing component.

* * * * *